United States Patent
Miller

(10) Patent No.: US 10,245,326 B2
(45) Date of Patent: Apr. 2, 2019

(54) AMANTADINE, MEMANTINE, AND RIMANTADINE CONJUGATES AND A PHARMACEUTICAL COMPOSITION FOR TREATMENT OF NEURONAL DISORDERS

(71) Applicant: Landon C. G. Miller, Tuscaloosa, AL (US)

(72) Inventor: Landon C. G. Miller, Tuscaloosa, AL (US)

( * ) Notice: Subject to any disclaimer, the term of this patent is extended or adjusted under 35 U.S.C. 154(b) by 0 days.

(21) Appl. No.: 14/819,959

(22) Filed: Aug. 6, 2015

(65) Prior Publication Data
US 2017/0035889 A1    Feb. 9, 2017

(51) Int. Cl.
*A61K 47/64*    (2017.01)

(52) U.S. Cl.
CPC ................... *A61K 47/64* (2017.08)

(58) Field of Classification Search
CPC .... A61K 31/131; A61K 31/133; A61K 31/16; A61K 31/164
See application file for complete search history.

(56) References Cited

U.S. PATENT DOCUMENTS

2005/0124701 A1*  6/2005  Went ............... A61K 47/48007
514/662

FOREIGN PATENT DOCUMENTS

CZ    277752 B6 *  3/1993

OTHER PUBLICATIONS

Kwapiszewski et al (Acta Poloniae Pharmaceutica (1974), 31(4), 457-61).*

Alex et al, RSC Drug Discovery Series No. 1, 2010, pp. 1-60.*

* cited by examiner

*Primary Examiner* — Sudhakar Katakam
(74) *Attorney, Agent, or Firm* — Avery N. Goldstein; Blue Filament Law PLLC

(57) ABSTRACT

A compound is provided that has the formula (II):

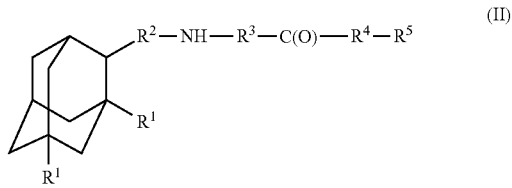

where $R^1$ in each occurrence is independently H, or $C_1$-$C_4$ alkyl; $R^2$ is a nullity or CH—$CH_3$, $R^3$ is a nullity or C(O)—$R^6$—NH; $R^6$ is $C_2$-$C_6$ alkyl, $(CH_2CH_2—O)_n$, or $(CH(OH)CH_2)_n$; n is an integer of between 1 and 4; $R^4$ is a nullity or NH—$R^6$—C(O); and $R^5$ is a moiety capable of crossing the blood brain barrier and is as a free compound serotonin, dopamine, blood brain barrier (BBB) peptide, membrane translocating peptide, TAT peptides, endocannabinoids 1 & 2, bradykinin, beta-endorphin, bombesin, calcitonin, cholecystokinin, an enkephalin, dynorphin, insulin, gastrin, substance P, neurotensin, glucagon, secretin, somatostatin, motilin, vasopressin, oxytocin, prolactin, thyrotropin, an angiotensin, galanin, neuropeptide Y, thyrotropin-releasing hormone, gonadotropin-releasing hormone, growth hormone-releasing hormone, luteinizing hormone, vasoactive intestinal peptide transferrin, glucosyl ester, lactic acid, leucine, tryptophan, glutamic acid.

10 Claims, No Drawings

AMANTADINE, MEMANTINE, AND RIMANTADINE CONJUGATES AND A PHARMACEUTICAL COMPOSITION FOR TREATMENT OF NEURONAL DISORDERS

FIELD OF THE INVENTION

The subject invention relates to a amantadine or amantadine analog conjugate and synthesis thereof and, more specifically, to the treatment of neuronal disorders by administering the amantadine or amantadine analog conjugate.

BACKGROUND OF THE INVENTION

Amantadine and related compounds have been shown to moderate dopamine levels in the brain and also to have certain activity as antivirals. Additionally, these compounds have activity in the treatment of Parkinson's disease. Generally, amantadine and amantadine analogs have fallen out of favor as therapeutics owing to many strains of influenza virus being refractory towards these compounds, while as an anti-Parkinsonian drug side effects outweighed clinical efficacy. Nonetheless, amantadine and a amantadine analogs are antagonist of the NMDA-type glutamate receptor, increases dopamine release, and blocks dopamine reuptake.

Amantadine and amantadine analogs create CNS side effects of nervousness, anxiety, agitation, insomnia, and accentuate pre-existing seizure disorders and psychiatric symptoms in patients with schizophrenia or Parkinson's disease. The need to screen patients for a history of seizures and psychiatric symptoms in an effort to preclude such side effects has also limited use of amantadine and amantadine analogs. The aliphatic and rigid structure of the adamantane core of these therapeutics with a single polar amine functionality makes these compounds prone to segregation in a phospholipid bilayer with the amine moiety oriented with the polar phosphate groups of the bilayer and the adamantane core within the lipid portion of the bilayer. As a result, the ability of ability of amantadine and amantadine analogs to transit the blood brain barrier and provide therapeutic effect is limited, while the propensity to cause side effects through cellular membrane disruption is high.

Thus, there exists a need for an improved composition for systemic and/or intrathecal delivery of amantadine and its analogs that mitigate side effects.

SUMMARY OF THE PRESENT INVENTION

A compound is provided that has the formula (II):

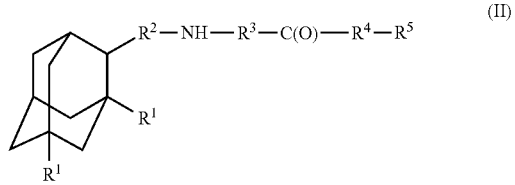

where $R^1$ in each occurrence is independently H, or $C_1$-$C_4$ alkyl; $R^2$ is a nullity or CH—$CH_3$, $R^3$ is a nullity or C(O)—$R^6$—NH; $R^6$ is $C_2$-$C_6$ alkyl, $(CH_2CH_2$—$O)_n$, or (CH(OH)$CH_2)_n$; n is an integer of between 1 and 4; $R^4$ is a nullity or NH—$R^6$—C(O); and $R^5$ is a moiety capable of crossing the blood brain barrier and is as a free compound serotonin, dopamine, blood brain barrier (BBB) peptide, membrane translocating peptide, TAT peptides, bradykinin, beta-endorphin, bombesin, calcitonin, cholecystokinin, an enkephalin, dynorphin, insulin, gastrin, substance P, neurotensin, glucagon, secretin, somatostatin, motilin, vasopressin, oxytocin, prolactin, thyrotropin, an angiotensin, galanin, neuropeptide Y, thyrotropin-releasing hormone, gonadotropnin-releasing hormone, growth hormone-releasing hormone, luteinizing hormone, vasoactive intestinal peptide transferrin, glucosyl ester, lactic acid, leucine, tryptophan, glutamic acid, or endocannabinoid 1 or 2. The compound traverses the blood brain barrier with greater efficiency than amantadine or amantadine analogs thereby reducing side effects associated with systemic amantadine or the corresponding amantadine analog therapy. A process for forming a conjugate having the formula (II) illustratively includes reacting amantadine or an amantadine analog amine moiety with an acid moiety, and acid chloride, or ester of a transporter molecule able to traverse the blood brain barrier. The transporter molecule includes serotonin, dopamine, blood brain barrier (BBB) peptide, TAT peptide, glucosyl ester, lactic acid, leucine, tryptophan, glutamic acid, bradykinin, beta-endorphin, bombesin, calcitonin, cholecystokinin, an enkephalin, dynorphin, insulin, gastrin, substance P, neurotensin, glucagon, secretin, somatostatin, motilin, vasopressin, oxytocin, prolactin, thyrotropin, an angiotensin, galanin, neuropeptide Y, thyrotropin-releasing hormone, gonadotropnin-releasing hormone, growth hormone-releasing hormone, luteinizing hormone, vasoactive intestinal peptide transferrin, so as to form an amide bond. The acid, acid chloride or ester of the transporter molecule reacts with the amantadine or amantadine analog amine moiety to form an amide bond. A spacer group $R^3$, $R^4$ or a combination thereof are present in some embodiments of the invention to include a detectable moiety or an enzymatic cleavage site between the transporter molecule and the amantadine or amantadine analog amine moiety.

DETAILED DESCRIPTION OF THE INVENTION

The present invention provides a method for treating neuronal conditions or disorders often associated with Parkinson's disease, viral infections, multiple sclerosis complications, and providing neuro-protection against the results of concussive or direct traumatic injury to both the peripheral and the central nervous system, including the brain, by administration to a patient or subject having the condition or disorder a therapeutically effective amount of amantadine or amantadine analog conjugate that is able to cross the blood-nerve barrier. Adjunct therapies for facilitating such transport are also provided.

The term "amantadine analog" includes those molecules that contain an adamantane ring having an amine moiety extending from the ring and a molecular weight of less than 350 and a therapeutic effect in a subject and specifically includes memantine, and rimantadine and illustrated with respect to formula (I) where variables have the structures detailed with respect to formula (II):

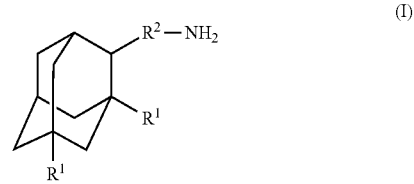

The terms "patient" and "subject" are synonymous and mean all animals including humans. Examples of patients or subjects include humans, cows, dogs, cats, goats, sheep, and pigs.

The term "solubility products" means those compounds or compositions formed when a compound is disposed in a solvent.

Those skilled in the art are easily able to identify patients or subjects having Parkinson's disease, viral infections, or multiple sclerosis through routine clinical tests.

A therapeutically effective amount is defined as an amount of a amantadine or amantadine analog conjugate that when administered to a patient or subject, ameliorates a symptom of the condition or disorder.

The compounds of the present invention can be administered to a patient either alone, as part of a pharmaceutical composition, or as part of a closed loop detection, monitoring, and amelioration system. The inventive compositions are suitable for administration to patients by a variety of routes including intrathecally, intraventricularly, intravenously, orally, parenterally, and mucosally.

Compositions suitable for delivery illustratively include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers; diluents; solvents; or vehicles include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of the required particle size in the case of dispersions, and by the use of surfactants.

A compound is provided that has the formula (II):

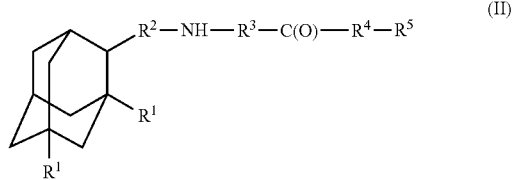

where $R^1$ in each occurrence is independently H, or $C_1$-$C_4$ alkyl; $R^2$ is a nullity or CH—$CH_3$, $R^3$ is a nullity or C(O)—$R^6$—NH; $R^6$ is $C_2$-$C_6$ alkyl, $(CH_2CH_2—O)_n$, or $(CH(OH)CH_2)_n$; n is an integer of between 1 and 4; $R^4$ is a nullity or NH—$R^6$—C(O); and $R^5$ is a moiety capable of crossing the blood brain barrier and is as a free compound serotonin, dopamine, blood brain barrier (BBB) peptide, membrane endocannabinoids 1 & 2 translocating peptide, TAT peptides, bradykinin, beta-endorphin, bombesin, calcitonin, cholecystokinin enkephalin dynorphin, insulin, gastrin, substance P, neurotensin, glucagon, secretin, somatostatin, motilin, vasopressin, oxytocin, prolactin, thyrotropin, an angiotensin, galanin, neuropeptide Y, thyrotropin-releasing hormone, gonadotropin-releasing hormone growth hormone-releasing hormone, luteinizing hormone, vasoactive intestinal peptide transferrin, glucosyl ester, lactic acid, leucine, tryptophan, glutamic acid. The compound traverses the blood brain barrier with greater efficiency than amantadine or amantadine analogs thereby reducing side effects associated with systemic amantadine or the corresponding amantadine analog therapy. A process for forming a conjugate having the formula (II) illustratively includes reacting amantadine or an amantadine analog amine moiety with an acid moiety, and acid chloride, or ester of a transporter molecule able to traverse the blood brain barrier. The transporter molecule includes serotonin, dopamine, blood brain barrier (BBB) peptide, TAT peptide, glucosyl ester, lactic acid, leucine, tryptophan, glutamic acid, bradykinin, beta-endorphin, bombesin, calcitonin, cholecystokinin, an enkephalin, dynorphin, insulin, gastrin, substance P, neurotensin, glucagon, secretin, somatostatin, motilin, vasopressin, oxytocin, prolactin, thyrotropin, an angiotensin, galanin, neuropeptide Y, thyrotropin-releasing hormone, gonadotropnin-releasing hormone, growth hormone-releasing hormone, luteinizing hormone, vasoactive intestinal peptide transferrin, so as to form an amide bond. The acid chloride or ester of the transporter molecule reacts with the amantadine or amantadine analog amine moiety to form an amide bond. A spacer group is present in some embodiments of the invention to include a detectable moiety or an enzymatic cleavage site between the transporter molecule and the amantadine or amantadine analog amine moiety.

An inventive compound being formed preferably through the reaction of an amantadine or amantadine analog amine with a carboxy group, or an ester from the carboxyl group of a transporter, or an acid chloride from the carboxyl group of a transporter. A linker is optionally included of $R^3$, $R^4$, or both through convention amide bond conjugation to impart a spacer or spectroscopically detectable dye or marker.

According to the present invention, an amantadine or amantadine analog conjugate compound is formed to a species known to traverse the blood brain barrier either through diffusion or a specific transporter. White the specific transport mechanism is unclear, owing to the small molecular weight and lack of steric hindrance associated with amantadine or amantadine analog, inhibitory effects on the transporter species associated with conjugation are limited.

In a preferred embodiment, an inventive conjugate compound includes a transporter moiety $R^5$ having a privileged ability to pass the blood brain barrier and thereafter be cleaved from a amantadine or amantadine analog component to itself form an active therapeutic or neurochemistry equilibrium modifier. The ability to deliver as a conjugate an amantadine or amantadine analog with a second neuroactive species provides a previously unavailable ability to moderate a neurological therapeutic effect. As neuroactive compounds are subject to complex feedback mechanisms, the successful transport of a compound across the blood brain barrier has a moderated therapeutic effect owing to neurochemistry equilibrium shifts in response to the compound traversing the barrier. An inventive conjugate provides amantadine or amantadine analog that upon cleavage from the transporter moiety $R^5$ is in proximity to a second neurologically active species that has an agonistic, antagonistic, or independently operating neuroactive species. The amantadine or amantadine analog and moiety $R^6$ after cleavage being subject to further enzymatic modification and/or efflux clearance. It is appreciated that two or more inventive conjugates are amenable to simultaneous delivery in order to provide still more refined therapeutic effects.

An inventive conjugate compound is preferably formed through an amide linkage between an amantadine or amantadine analog primary amine and an ester or carboxylic acid of a blood brain barrier transporter compound. Blood brain barrier transporter compounds operative herein illustratively include serotonin, blood brain barrier (BBB) peptide, membrane translocating peptide, endocannabinoids 1 & 2 dopamine, transferrin, TAT peptides, bradykinin, beta-endorphin, bombesin, calcitonin, cholecystokinin enkephalin dynorphin, insulin, gastrin, substance P, neurotensin, glucagon, secretin, somatostatin, motilin, vasopressin, oxytocin, prolactin, thyrotropin, an angiotensin, galanin, neuropeptide Y, thyrotropin-releasing hormone, gonadotropnin-releasing hormone, growth hormone-releasing hormone, luteinizing hormone, vasoactive intestinal peptidegluconate, a glucose ester, L-lactic acid, L-leucine, and L-glutamate. The transporter compound carboxyl moiety, ester thereof or acid chloride thereof is reacted with an amantadine or amantadine amine to form an amide bond.

Carbodiimides are zero length cross-linkers that mediate the formation of an amide or phosphoramidate linkage between a carboxylate and an amine, or a phosphate and an amine, respectively. Chu, B., Kramer, F. & Orgel, L. (1986), "Synthesis of an amplifiable reporter RNA for bioassays," Nucleic Acids Research, 14, 5591-5603. Hoare, D. and Koshland, D. E. (1966) J. Am. Chem. Soc., 88, 2057. Carbodiimides react with carboxylic acids to form highly reactive O-acylisourea compounds that are very short lived but react with nucleophiles to form an amide bond. Dicyclohexylcarbodiimide (DCCD) is representative of a reactive carbodiimide. This reaction works effectively between pH 4.5 and 7.5. Molecules with a phosphate group such as the 5' phosphate on oligonucleotides can also react with amine-containing groups by using the carbodiimide reaction. Alternatively, direct reaction of the transporter acid moiety and the amine moiety of the amantadine or amantadine analog is accomplished at room temperature in water in the presence of a boronic acid catalyst as detailed in Ishihara, K., Ohara, S. and Yamamoto, H. 3,4,5-Trifluorobenzeneboronic acid as an extremely active amidation catalyst. *J. Org. Chem.* 61, 4196-4197 (1996).

Optionally, a linker species, used for additive purposes, is provided as an intermediate between the transporter moiety $R^6$ and the amide bond of an inventive conjugate. The linker in simplest form includes a moiety reactive with the pendant carbonyl carbon of the transporter compound and a second moiety reactive with the amantadine or amantadine analog precursor amine. Substituents extending from a linker are provided to modify the lipophilicity of an inventive conjugate, or tether a dye or spectroscopic marker. With the inclusion of a linker, care should be taken to limit both the molecular weight and the hydrophilicity of the linker in order to retain the ability to traverse the blood brain barrier. Typically, the linker has eight or less backbone carbon atoms. Preferably, the linker backbone is linked to the amantadine or amantadine analog amido portion of an inventive conjugate compound through an oxygen atom or a carbon atom. The linker moiety reactive with the transporter portion carbonyl carbon illustratively form an amide and an ester linkage. Suitable chemistries for a variety of potential reaction moieties are found in *Comprehensive Organic Transformations*, R. C. Larock, John Wiley & Sons 1999.

It is appreciated that a linker, $R^3$, $R^4$, or both, when present, is the preferred site for an additive feature such as the attachment of an additional species. A substituent is optionally provided pendent from the linker backbone. The substituent illustratively includes a radioactive atom, a magnetic spectroscopically active marker and an organic dye. A radioactive atom is alternatively operative as a marker in isotope studies such as positron emission tomography, single photon emission computer tomography, radiological studies and the like. Common radio-isotopes used in medical imaging illustratively include $^{123}$I, $^{99m}$Tc, and other chelated radioisotopes as detailed in U.S. Pat. No. 6,241,963. Spectroscopically active markers include NMR/MRI active contrast enhancing moieties known to the art such as gadolinium, as detailed in Contrast Agents 1: Magnetic Resonance Imaging (Topics in Current Chemistry, 221) by Werner Krause, Springer Verlag, Berlin, Germany. Organic dyes, while recognized to have potentially distinct NMR/MRI signatures, are provided to yield an optically active spectroscopic signature suitable for biopsy, surgical identification, or preclinical studies of tissue treated by an inventive compound.

Compositions suitable for injection optionally include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

The enteric coating is typically a polymeric material. Preferred enteric coating materials have the characteristics of being bioerodible, gradually hydrolyzable and/or gradually water-soluble polymers. The amount of coating material applied to a solid dosage generally dictates the time interval between ingestion and drug release. A coating is applied with to a thickness such that the entire coating does not dissolve in the gastrointestinal fluids at pH below 5 associated with stomach acids, yet dissolves above pH 5 in the small intestine environment. It is expected that any anionic polymer exhibiting a pH-dependent solubility profile is readily used as an enteric coating in the practice of the present invention to achieve delivery of the active to the lower gastrointestinal tract. The selection of the specific enteric coating material depends on properties such as resistance to disintegration in the stomach; impermeability to gastric fluids and active agent diffusion while in the stomach; ability to dissipate at the target intestine site; physical and chemical stability during storage; non-toxicity; and ease of application.

Suitable enteric coating materials illustratively include cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropyhnethyl cellulose succinate and carboxymethylcellulose sodium; acrylic acid polymers and copolymers, preferably formed from acrylic acid, methacrylic acid, methyl acrylate, ammonio methylacrylate, ethyl acrylate, methyl methacrylate and/or ethyl; vinyl polymers and copolymers such as polyvinyl pyrrolidone, polyvinyl acetate, polyvinylacetate phthalate, vinyl acetate-crotonic acid copolymer, and ethylene-vinyl acetate copolymers; shellac; and combinations thereof. A particularly preferred enteric coating material for use herein are those acrylic acid polymers and copolymers available under the tradename EUDRAGIT®, Roehm Pharma (Germany). The EUDRAGIT® series L, L-30D and S copolymers are most preferred since these are insoluble in stomach and dissolve in the intestine.

The enteric coating provides for controlled release of the active agent, such that release is accomplished at a predictable location in the lower intestinal tract below the point at which drug release would occur absent the enteric coating. The enteric coating also prevents exposure of the active agent and carrier to the epithelial and mucosal tissue of the buccal cavity, pharynx, esophagus, and stomach, and to the enzymes associated with these tissues. The enteric coating therefore helps to protect the active agent and a patient's internal tissue from any adverse event prior to drug release at the desired site of delivery. Furthermore, the coated solid dosages of the present invention allow optimization of drug absorption, active agent protection, and safety. Multiple enteric coatings targeted to release the active agent at various regions in the lower gastrointestinal tract would enable even more effective and sustained improved delivery throughout the lower gastrointestinal tract.

The enteric coating optionally contains a plasticizer to prevent the formation of pores and cracks that allow the penetration of the gastric fluids into the solid dosage. Suitable plasticizers illustratively include, triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, a coating composed of an anionic carboxylic acrylic polymer typically contains approximately 10% to 25% by weight of a plasticizer, particularly dibutyl phthalate, polyethylene glycol, triethyl citrate and triacetin. The coating can also contain other coating excipients such as detackifiers, antifoaming agents, lubricants (e.g., magnesium stearate), and stabilizers (e.g., hydroxypropylcellulose, acids and bases) to solubilize or disperse the coating material, and to improve coating performance and the coated product.

The enteric coating is applied to a solid dosage using conventional coating methods and equipment. For example, an enteric coating can be applied to a solid dosage using a coating pan, an airless spray technique, fluidized bed coating equipment, or the like. Detailed information concerning materials, equipment and processes for preparing coated dosage forms may be found in Pharmaceutical Dosage Forms: Tablets, eds. Lieberman et al. (New York: Marcel Dekker, Inc., 1989), and in Ansel et al., Pharmaceutical Dosage Forms and Drug Delivery Systems, 6.sup.th Ed. (Media, Pa.: Williams & Wilkins, 1995).

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

The examples presented below are intended to illustrate particular embodiments of the invention and are not intended to limit the scope of the specification, including the claims.

EXAMPLES

Example 1

Preparation of glutamyl-1-amidyl-adamatitine

A mixture of 1-adamantine (5 mmol) and glutamic acid (5 mmol) are reacted in water at 25° C. in the presence of 3,4,5-Trifluorobenzeneboronic acid 5 mol % of glutamic acid for 24 hours. Ishihara, K., Ohara, S. and Yamamoto, H. 3,4,5-Trifluorobenzeneboronic acid as an extremely active amidation catalyst. *J. Org. Chem.* 61, 4196-4197 (1996). The resulting glutamyl-1-adamantine is collected and purified to pharmaceutical purity.

Example 2

Preparation of BBB peptide-1-amidyl-Amantadine

The procedure of Example 1 is repeated with BBB peptide in place of glutamic acid to yield the title compound at pharmaceutical purity.

Example 3

Preparation of BBB-peptide-amidyl-rimantidine

The procedure of Example 2 is repeated with the substitution of a stoichiometric amount of rimantidine for amantine to produce the title compound.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A method of treating Parkinson's disease, the method comprising:
   administration to subject having Parkinson's disease, a therapeutically effective amount of an amantadine analog conjugate compound having the formula (II):

$$R^2-NH-R^3-C(O)-R^4-R^5 \quad (II)$$

(with adamantane core bearing $R^1$, $R^1$)

where $R^1$ in each occurrence is independently H, or $C_1$-$C_4$ alkyl; $R^2$ is a nullity or $CH-CH_3$, $R^3$ is a nullity or $C(O)-R^6-NH$; $R^6$ is $C_2$-$C_6$ alkyl, $(CH_2CH_2-O)_n$, or $(CH(OH)CH_2)_n$; n is an integer of between 1 and 4; $R^4$ is a nullity or $NH-R^6-C(O)$; and $R^5$ is a moiety capable of crossing the blood brain barrier and is as a free compound is one of: serotonin, dopamine, blood brain barrier (BBB) peptide, membrane translocating peptide, TAT peptides, endocannabinoids, bradykinin, beta-endorphin, bombesin, calcitonin, cholecystokinin, an enkephalin, dynorphin, insulin, gastrin, substance P, neurotensin, glucagon, secretin, somatostatin, motilin, vasopressin, oxytocin, prolactin, thyrotropin, an angiotensin, galanin, neuropeptide Y, thyrotropin-releasing hormone, gonadotropnin-releasing hormone, growth hormone-releasing hormone, luteinizing hormone, vasoactive intestinal peptide transferrin, glucosyl ester, lactic acid, leucine, tryptophan, glutamic acid.

2. The method of claim 1, wherein $R^5$ is serotonin as the free compound and has a carboxyl group that forms an amide bond.

3. The method of claim 1, wherein $R^5$ is glucosyl, $R^3$ is a nullity and $R^4$ is a nullity.

4. The method of claim 1, wherein $R^5$ is transferrin as the free compound and has a carboxyl group that forms an amide bond.

5. The method of claim 1, wherein $R^5$ is lactic acid as the free compound and has a carboxyl group that forms an amide bond.

6. The method of claim 1, wherein at least one of $R^3$ and $R^4$ is $C(O)-R^6-NH$, where $R^6$ is $C_2$-$C_6$ alkyl, $(CH_2CH_2-O)_n$, or $(CH(OH)CH_2)_n$ and n is an integer of between 1 and 4.

7. The method of claim 6, wherein $R^6$ is $(CH_2CH_2-O)_n$, and n is an integer of between 1 and 4.

8. The method of claim 6, wherein $R^6$ is $(CH(OH)CH_2)_n$ and n is an integer of between 1 and 4.

9. The method of claim 6, further comprising at least one of a radioactive atom, a spectroscopically active marker, and an organic dye.

10. The method of claim 1, wherein the administration is by a route selected from the group consisting of: parenteral, intraventricular, and intrathecal.

* * * * *